(12) United States Patent
Imai

(10) Patent No.: US 10,088,668 B2
(45) Date of Patent: Oct. 2, 2018

(54) ENDOSCOPE

(71) Applicant: OLYMPUS CORPORATION, Tokyo (JP)

(72) Inventor: Shunichi Imai, Okaya (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/248,243

(22) Filed: Aug. 26, 2016

(65) Prior Publication Data

US 2016/0363757 A1    Dec. 15, 2016

Related U.S. Application Data

(63) Continuation of application No. PCT/JP2015/059113, filed on Mar. 25, 2015.

(30) Foreign Application Priority Data

Apr. 11, 2014    (JP) .................................. 2014-082270

(51) Int. Cl.
*A61B 1/00* (2006.01)
*A61B 1/05* (2006.01)
(Continued)

(52) U.S. Cl.
CPC ...... *G02B 23/2476* (2013.01); *A61B 1/00009* (2013.01); *A61B 1/00045* (2013.01);
(Continued)

(58) Field of Classification Search
CPC .............. A61B 1/00105; A61B 1/0011; A61B 1/00163; A61B 1/00174; A61B 1/00177;
(Continued)

(56) References Cited

FOREIGN PATENT DOCUMENTS

| JP | H11-056756 A | 3/1999 |
| JP | 2003-180621 A | 7/2003 |
| JP | 2013-128710 A | 7/2013 |

OTHER PUBLICATIONS

Imai, Shunichi (JP 2013-128710 A); Apr. 7, 2013 Date of Publication; English Translation Attached; Foreign Reference Provided by Applicant.*

(Continued)

*Primary Examiner* — John P Leubecker
*Assistant Examiner* — Pamela F Wu
(74) *Attorney, Agent, or Firm* — Scully, Scott, Murphy & Presser, P.C.

(57) ABSTRACT

An endoscope includes: a contact surface formed on a part of an outer circumference of a functional member; a distal end member provided on a distal end portion of the insertion portion and including a first hole portion provided with a first hole axis, in which the functional member is arranged, and a second hole portion provided with a second hole axis being orthogonal to the first hole axis and communicating with the first hole portion; and a fixing member configured to fix the functional member to the distal end member by being inserted into the second hole portion in a state that a contactless portion not being in contact with the contact surface is caused to face the contact surface, and being rotated around an axis by a predetermined angle.

10 Claims, 17 Drawing Sheets

(51) Int. Cl.
  *G02B 23/24* (2006.01)
  *A61B 1/005* (2006.01)
  *A61B 1/018* (2006.01)
  *A61B 1/06* (2006.01)
(52) U.S. Cl.
  CPC ............ *A61B 1/0052* (2013.01); *A61B 1/018* (2013.01); *A61B 1/05* (2013.01); *A61B 1/0661* (2013.01)
(58) Field of Classification Search
  CPC ............ A61B 1/00179; A61B 1/00181; A61B 1/00183; A61B 1/00186; A61B 1/00188; A61B 1/0019; A61B 1/00193; A61B 1/00195; A61B 1/00197; A61B 1/04; A61B 1/045; A61B 1/05; A61B 1/051; A61B 1/053; A61B 1/055; A61B 1/0676; A61B 1/00096; G02B 23/2476
  USPC ........................................................ 600/130
  See application file for complete search history.

(56) References Cited

OTHER PUBLICATIONS

International Search Report dated Jun. 16, 2015 issued in PCT/JP2015/059113.
Japanese Office Action dated Dec. 22, 2015 issued in JP 2015-547194.

\* cited by examiner

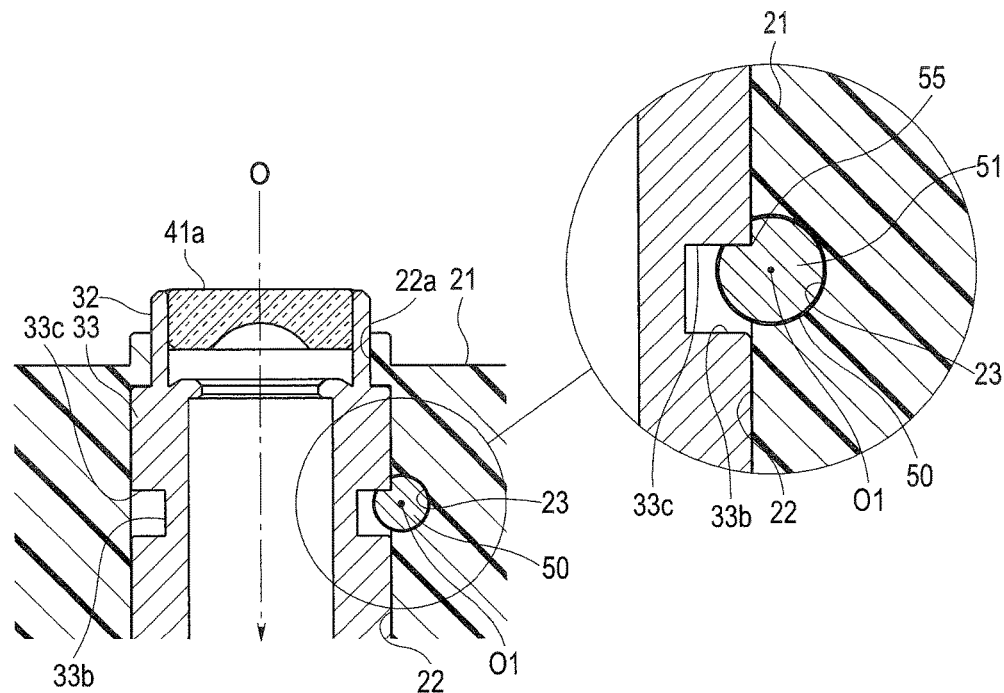
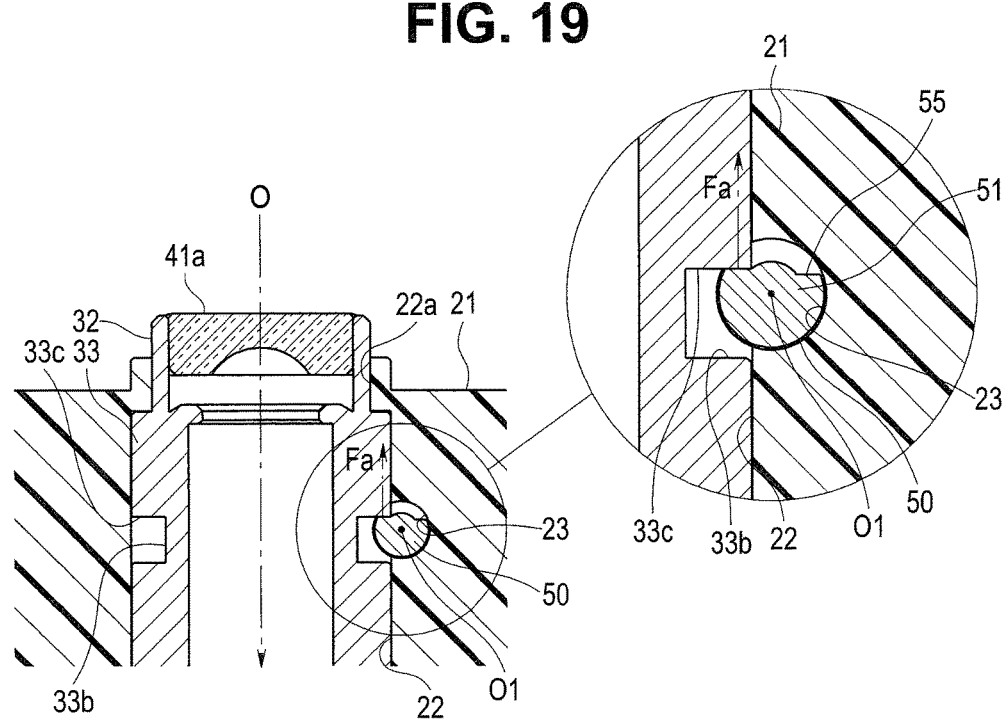

ENDOSCOPE

CROSS REFERENCE TO RELATED APPLICATION

This application is a continuation application of PCT/JP2015/059113 filed on Mar. 25, 2015 and claims benefit of Japanese Application No. 2014-082270 filed in Japan on Apr. 11, 2014, the entire contents of which are incorporated herein by this reference.

BACKGROUND OF THE INVENTION

1. Field of the Invention

The present invention relates to an endoscope in which various kinds of units are fixed to a distal end portion of an insertion portion.

2. Description of the Related Art

As is commonly known, endoscopes are widely used for observation, treatment and the like of an inside of a living body (an inside of a body cavity) or inspection, repair and the like of an inside of industrial plant facilities.

In such an endoscope, an image pickup unit in which an objective optical system is arranged, an illumination unit in which an illumination optical system is arranged, a channel unit for a treatment instrument channel, a nozzle unit for air/water feeding and the like are fixed to a distal end portion with screw members.

The various kinds of units are fixed by screwing screws into screw holes tapped in a distal end portion body, which is a distal end member provided on the distal end portion of the endoscope, and, furthermore, bonded and fixed so that the screws are not loosened.

Furthermore, recently, downsizing of the distal end portion has been promoted, accompanying diameter reduction for the insertion portion of the endoscope, and use of resin for the distal end portion body has been promoted from demands for complicated shape forming, integration, weight reduction and the like of the distal end portion.

When the distal end portion body is formed with resin as described above, there may be a case where the screw holes of a distal end rigid portion made of the resin are shaven and damaged by the screw members of fixing members for fixing the various kinds of units being screwed and removed at time of performing repair, maintenance and the like for the various units. When the screw holes of the distal end portion body are damaged, necessity for exchanging the distal end portion body of the endoscope occurs.

In order to prevent this, for example, Japanese Patent Application Laid-Open Publication No. 2013-128710 discloses a technique for an endoscope parts fixing structure which prevents fixed members from being damaged by fitting and removing fixing members.

In the conventional endoscope parts fixing structure, recess portions at a positions facing and overlapping with hole portions of a distal end portion body are formed on various kinds of units to be fitted to the distal end portion body on which the hole portions are formed, for example, an image pickup unit here; a projection portion to be engageably inserted into the recess portion of the image pickup unit is provided on a fixing member to be inserted into the hole portion of the distal end portion body; and, by rotating the fixing member so that the projection portion of the fixing member is shaved or deformed by wall surfaces forming the recess portion of the image pickup unit to be flattened, the image pickup unit is fixed to the distal end rigid portion.

SUMMARY OF THE INVENTION

An endoscope according to an aspect of the present invention includes: an insertion portion configured to be inserted into a subject; a functional member having a predetermined function; a contact surface formed on a part of an outer circumference of the functional member; a distal end member provided on a distal end portion of the insertion portion and including a first hole portion provided with a first hole axis, in which the functional member is arranged, and a second hole portion provided with a second hole axis being orthogonal to the first hole axis and extending in a tangential direction relative to an outer circumferential surface of the functional member arranged in the first hole portion and communicating with the first hole portion; and a fixing member configured to generate fixing force for fixing the functional member to the distal end member by being inserted into the second hole portion in a state that a contactless portion not being in contact with the outer circumferential surface is caused to face the outer circumferential surface, and being rotated around an axis by a predetermined angle.

BRIEF DESCRIPTION OF THE DRAWINGS

FIG. 18 relates to a second modification and is a partial cross-sectional view showing a state that the fixing pin fixed to the image pickup unit is inserted in the distal end constituting portion;

FIG. 19 relates to the second modification and is a partial cross-sectional view showing a state that the fixing pin is rotated, and the image pickup unit is fixed to the distal end constituting portion;

DETAILED DESCRIPTION OF THE PREFERRED EMBODIMENT(S)

An endoscope which is the present invention will be described below. Note that, in the description below, drawings based on each embodiment are schematic, and it should be noted that a relationship between thickness and width of each portion, a thickness ratio of respective portions, and the like are different from actual ones, and such parts that a mutual dimensional relationship and a ratio are different among the drawings may be included.

Note that, as for the endoscope in the description of a configuration below, the description will be made on a so-called flexible scope the insertion portion of which is flexible so as to be inserted into a digestive organ at an upper part or lower part of a living body as an example, the endoscope is not limited to the flexible scope. The technique is applicable to a so-called rigid scope with a rigid insertion portion used for surgical purposes.

First Embodiment

Figure 1:
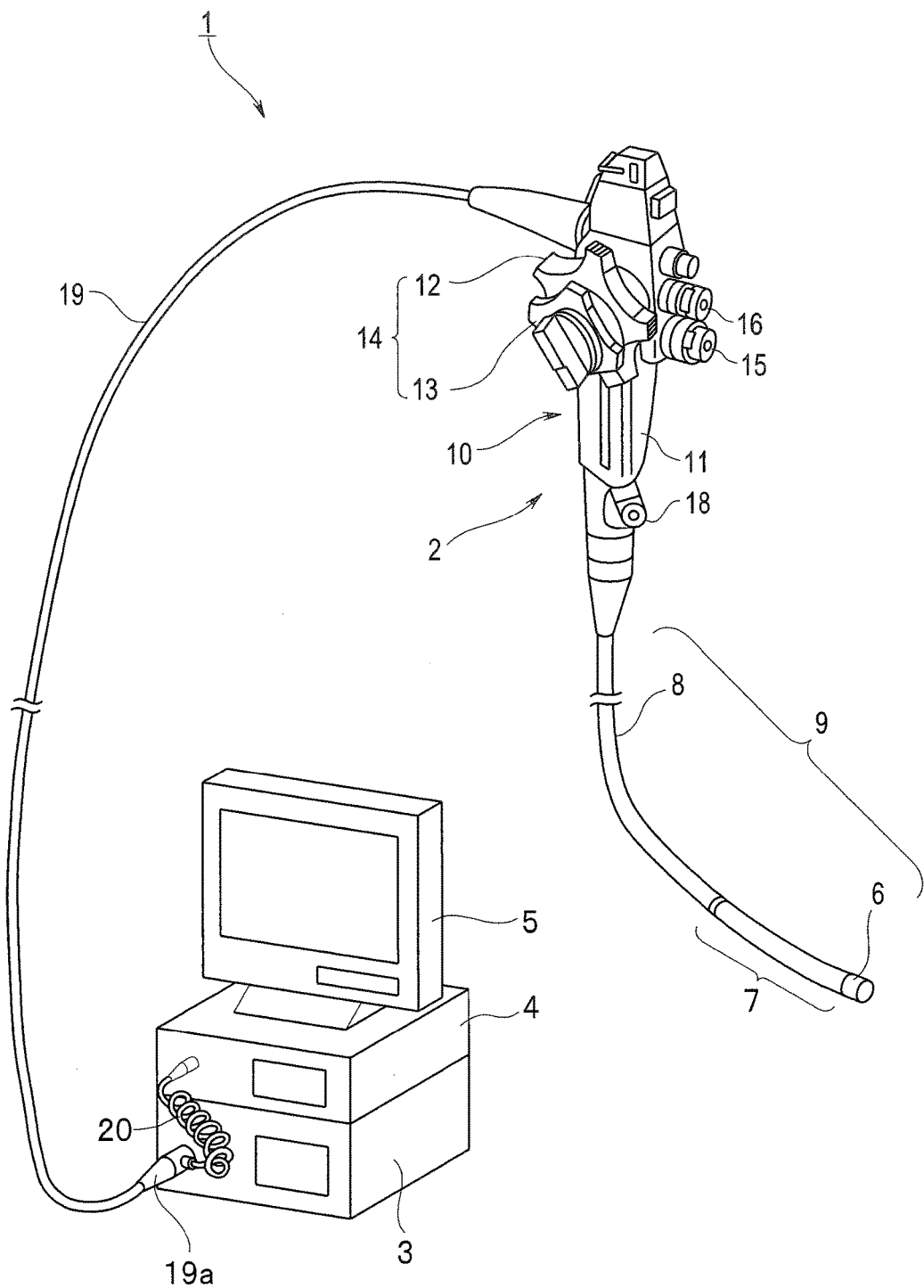
FIG. 1 is a perspective view showing a whole configuration of an endoscope apparatus according to an aspect of the present invention.
Figure 2:
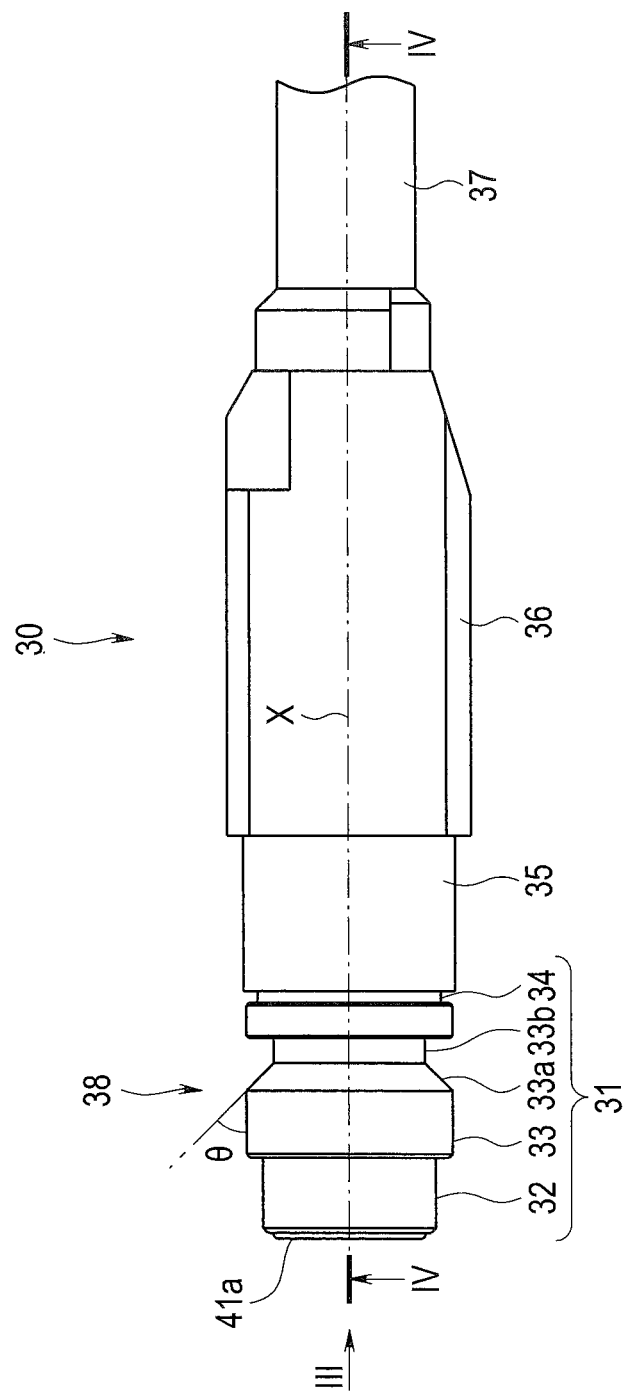
FIG. 2 is a side view of an image pickup unit according to the aspect of the present invention.
Figure 3:
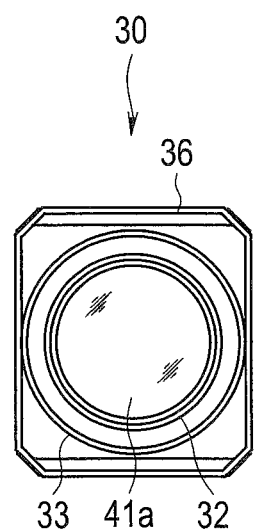
FIG. 3 is a front view of the image pickup unit of FIG. 2 seen from an arrow III according to the aspect of the present invention.
Figure 4:
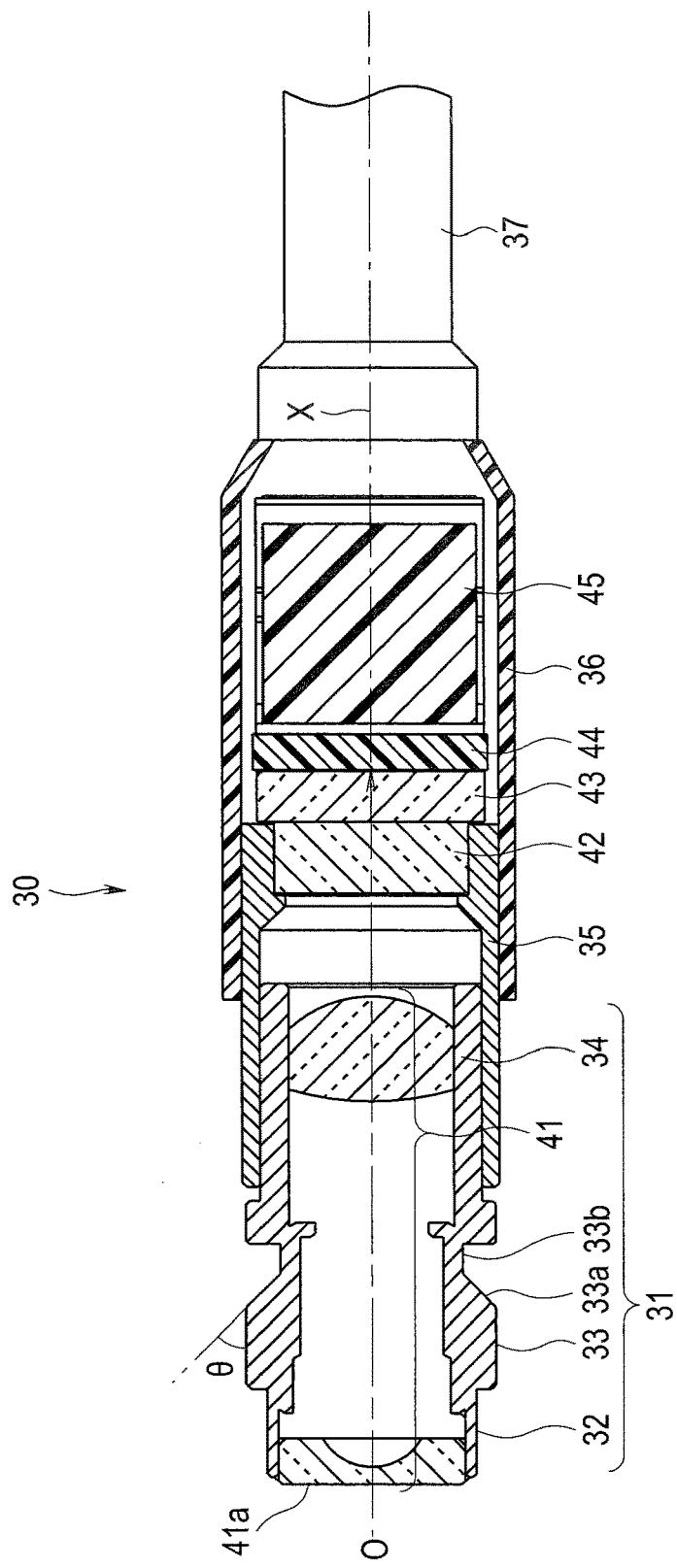
FIG. 4 is a IV-IV line cross-sectional view of the image pickup unit of FIG. 2 according to the aspect of the present invention.
Figure 5:
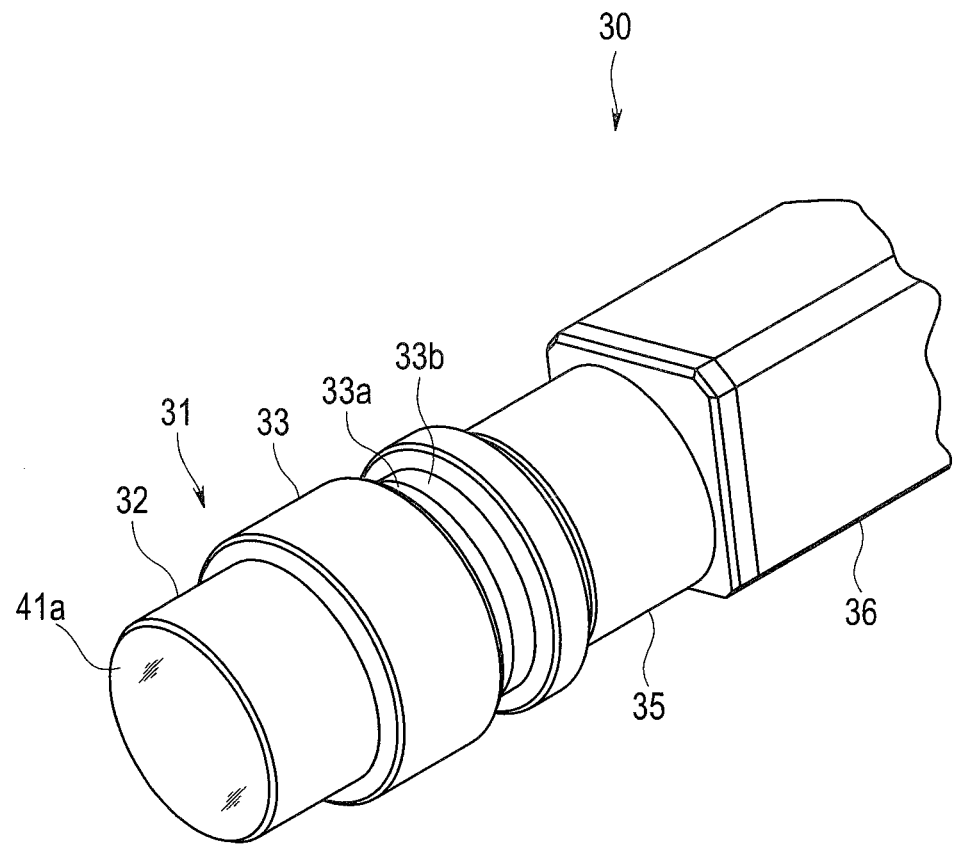
FIG. 5 is a perspective view showing a distal end portion of the image pickup unit according to the aspect of the present invention.
Figure 6:
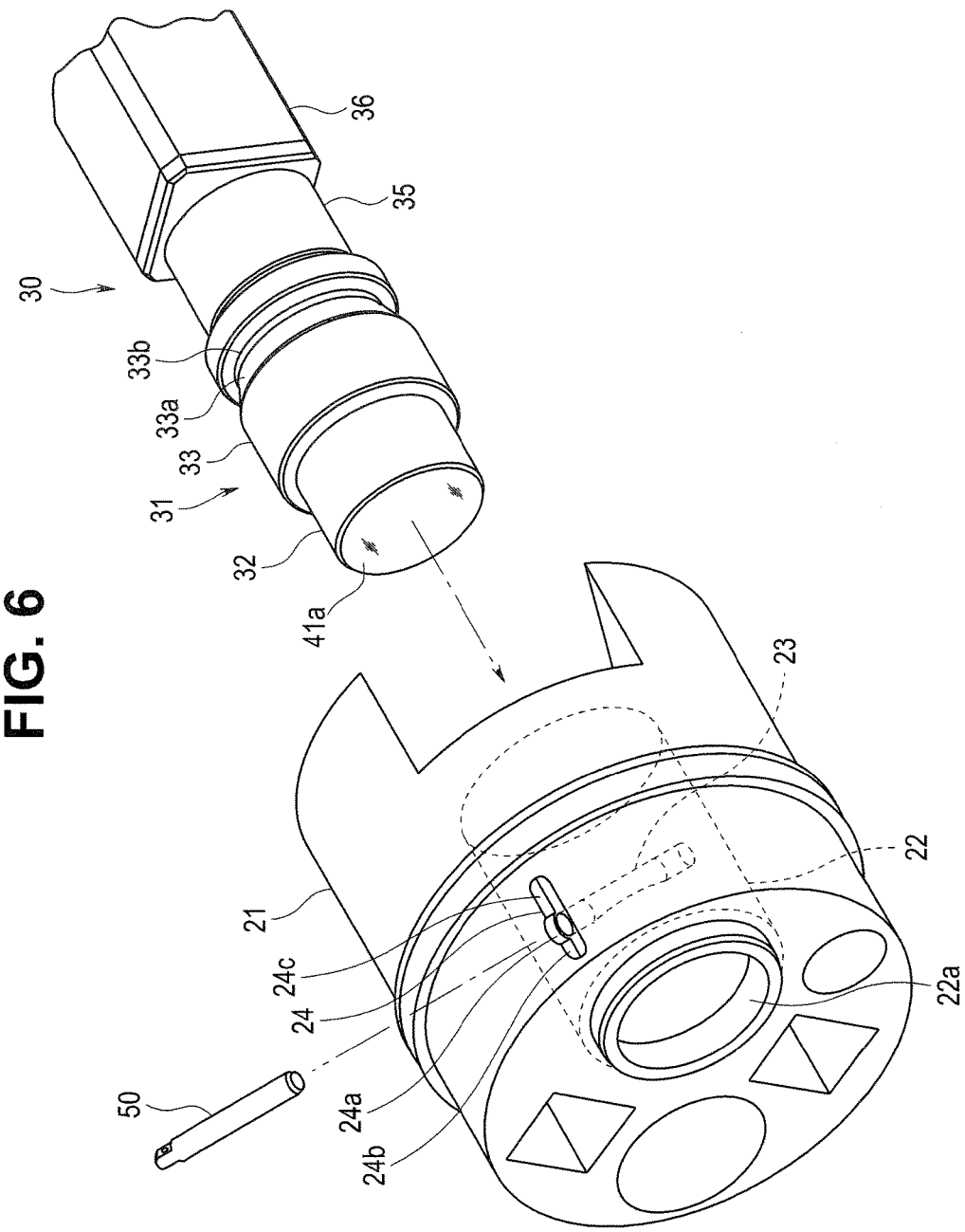
FIG. 6 is an exploded perspective view showing a state of fitting the image pickup unit to a distal end rigid portion, according to the aspect of the present invention.
Figure 7:
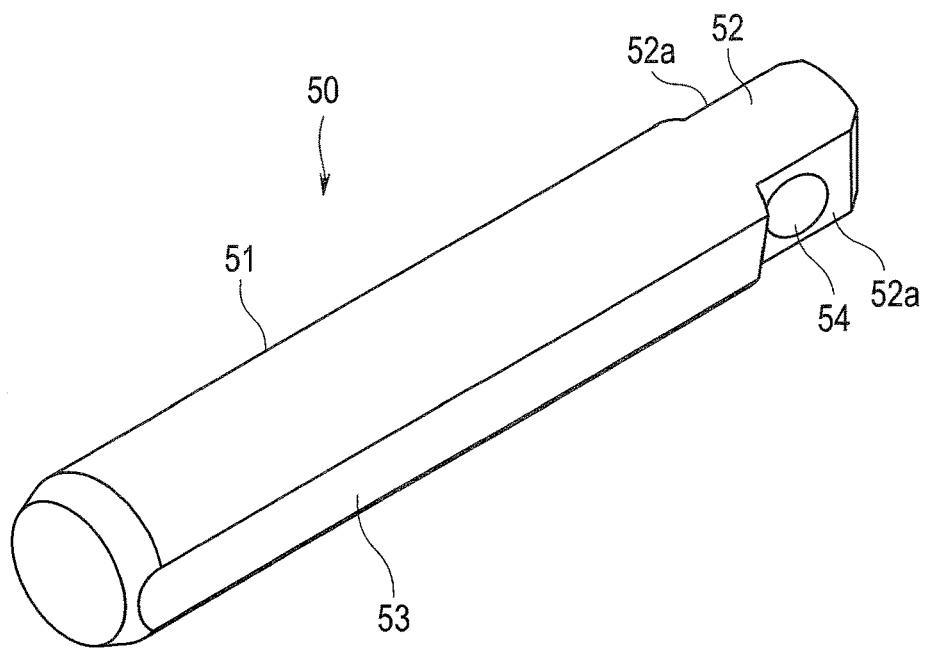
FIG. 7 is a perspective view showing a configuration of a fixing pin according to the aspect of the present invention.
Figure 8:
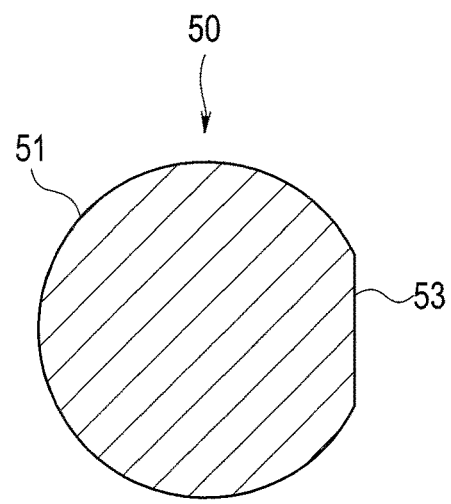
FIG. 8 is a cross-sectional view showing the configuration of the fixing pin according to the aspect of the present invention.
Figure 9:
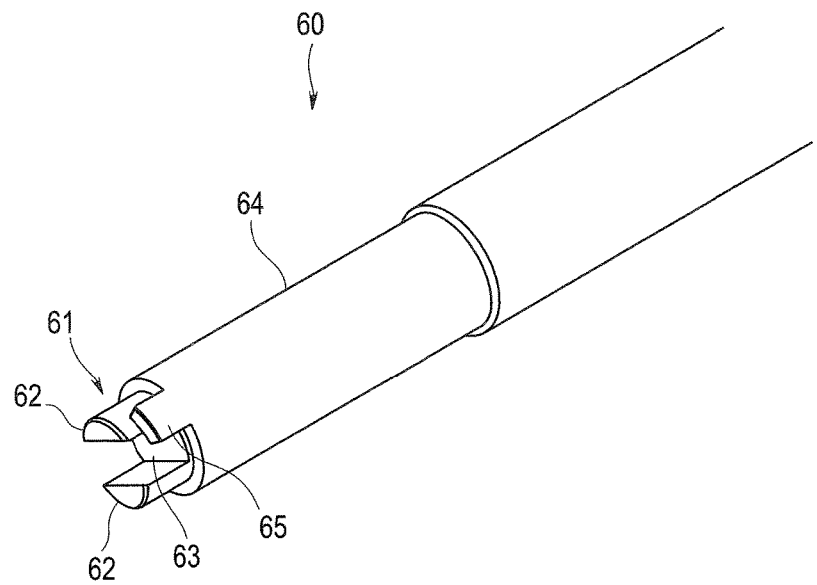
FIG. 9 is a perspective view showing a configuration of a jig according to the aspect of the present invention.
Figure 10:
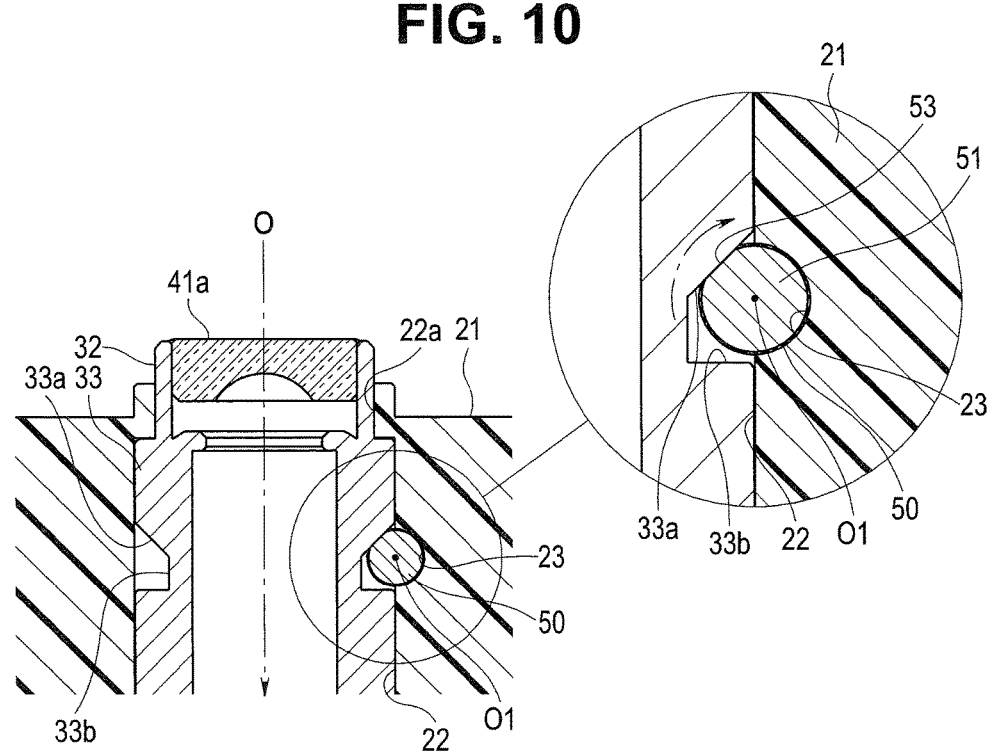
FIG. 10 is a partial cross-sectional view showing a state that the fixing pin to be fixed to the image pickup unit is inserted into a distal end constituting portion, according to the aspect of the present invention.
Figure 11:
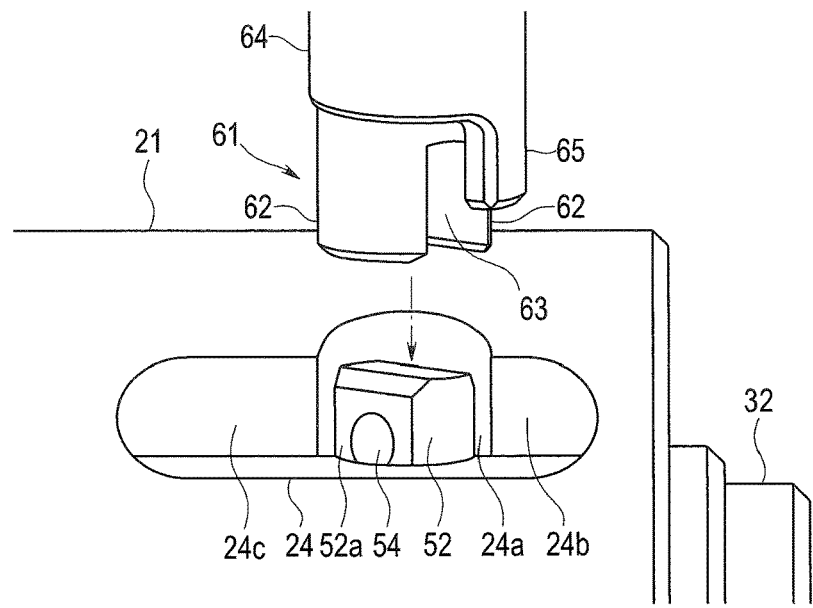
FIG. 11 is a perspective view showing a state before a head portion of the fixing pin projecting from a stepped portion of the distal end constituting portion is rotated with the jig, according to the aspect of the present invention.
Figure 12:
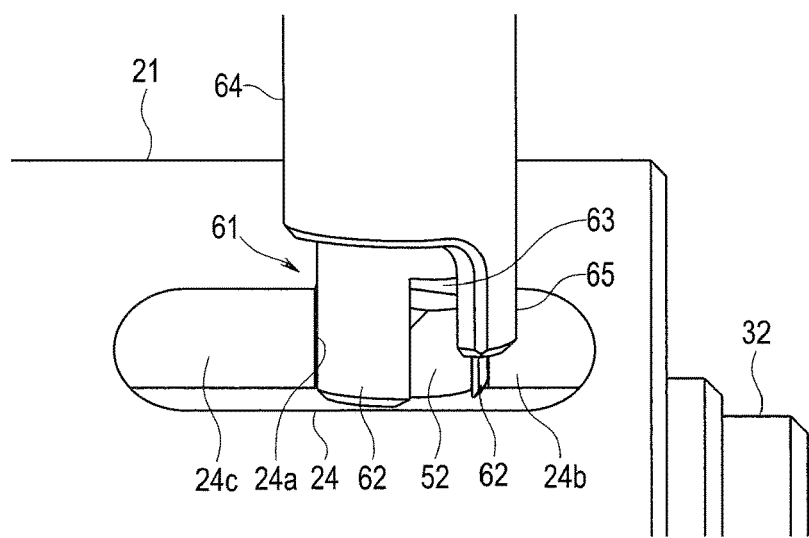
FIG. 12 is a perspective view showing a state that the jig is fitted in the head portion of the fixing pin, according to the aspect of the present invention.
Figure 13:
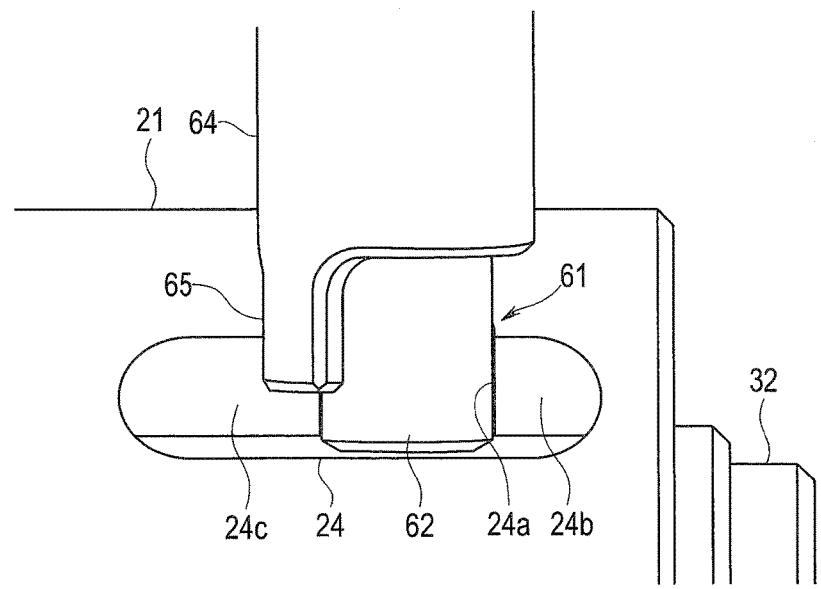
FIG. 13 is a perspective view showing a state that the fixing pin is rotated by the jig, according to the aspect of the present invention.
Figure 14:
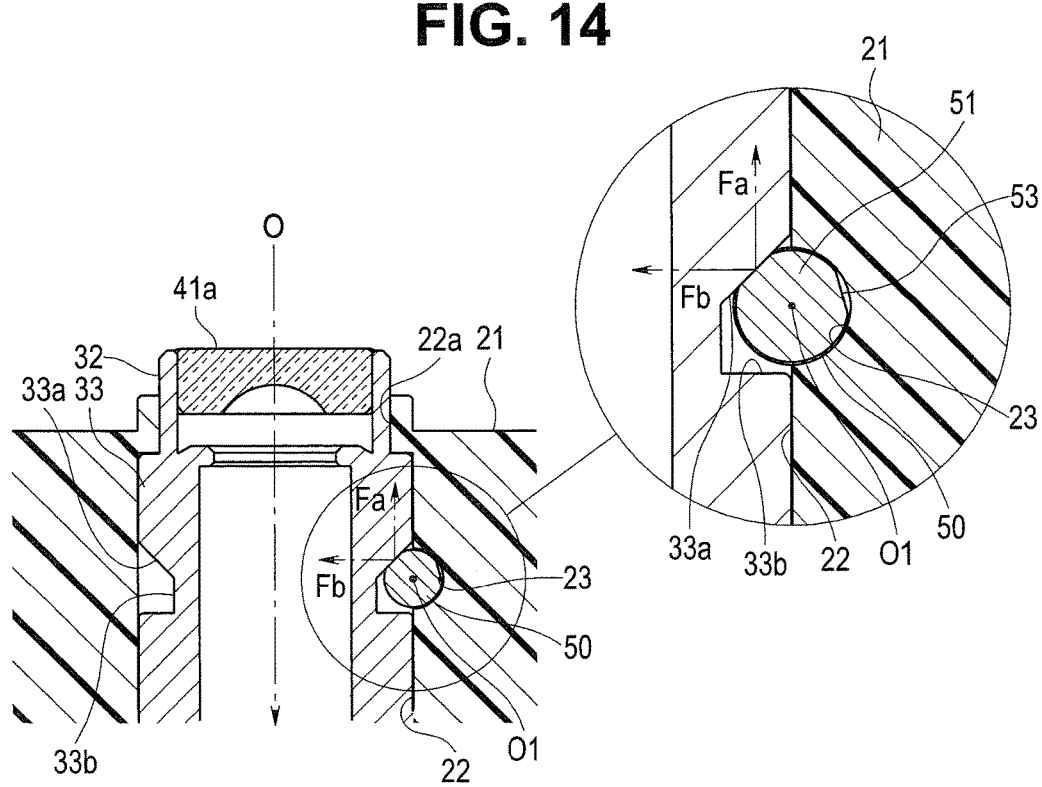
FIG. 14 is a partial cross-sectional view showing a state that the fixing pin is rotated, and the image pickup unit is fixed to the distal end constituting portion, according to the aspect of the present invention.
Figure 15:
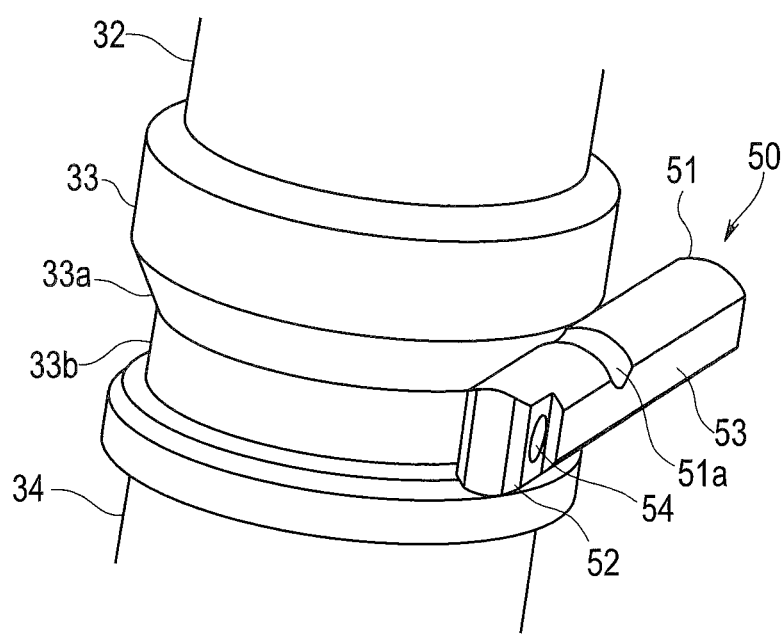
FIG. 15 is a perspective view showing a state that the image pickup unit is fixed with the fixing pin according to the aspect of the present invention.
Figure 16:
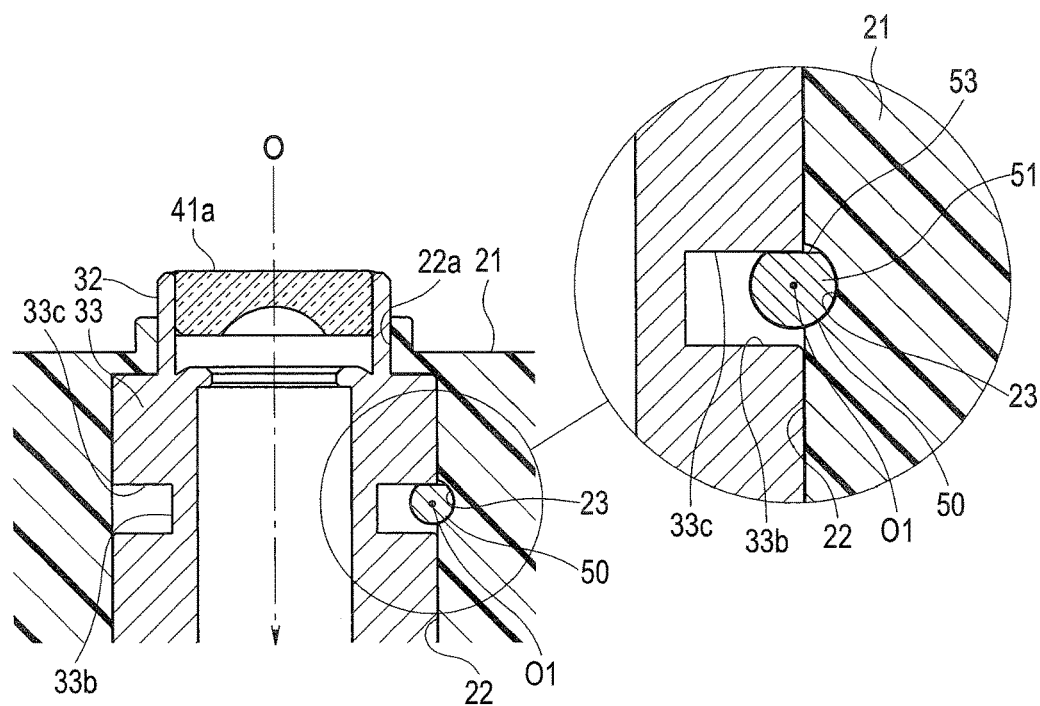
FIG. 16 relates to a first modification and is a partial cross-sectional view showing a state that the fixing pin fixed to the image pickup unit is inserted in the distal end constituting portion.
Figure 17:
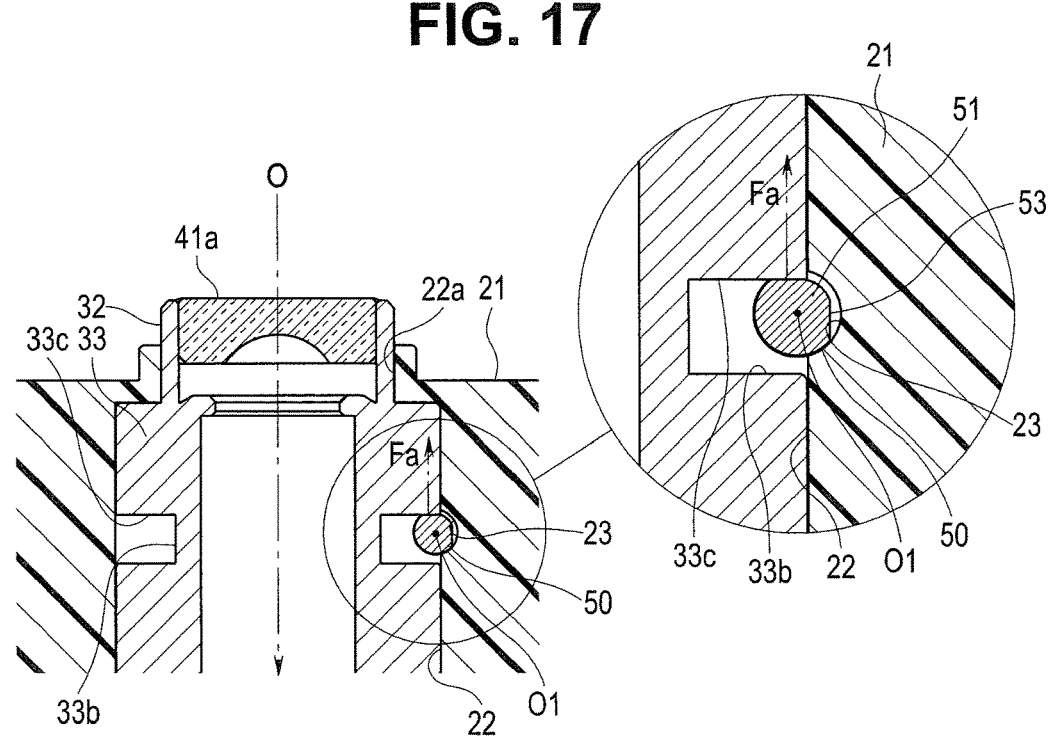
FIG. 17 relates to the first modification and is a partial cross-sectional view showing a state that the fixing pin is rotated, and the image pickup unit is fixed to the distal end constituting portion.
Figure 20:
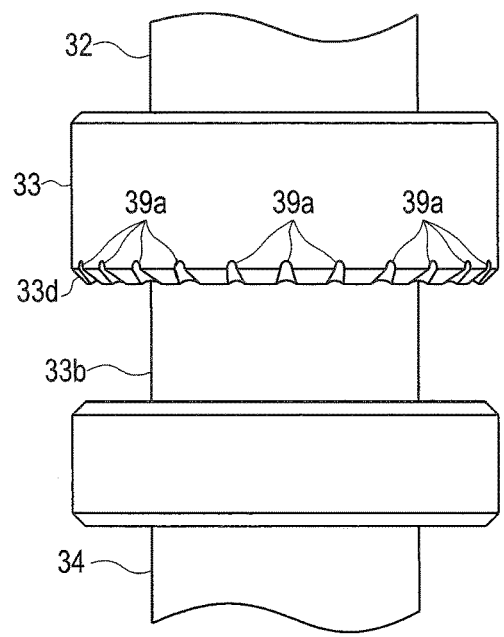
FIG. 20 relates to a third modification and is a side view showing a configuration of a body portion of a lens frame of the image pickup unit.
Figure 21:
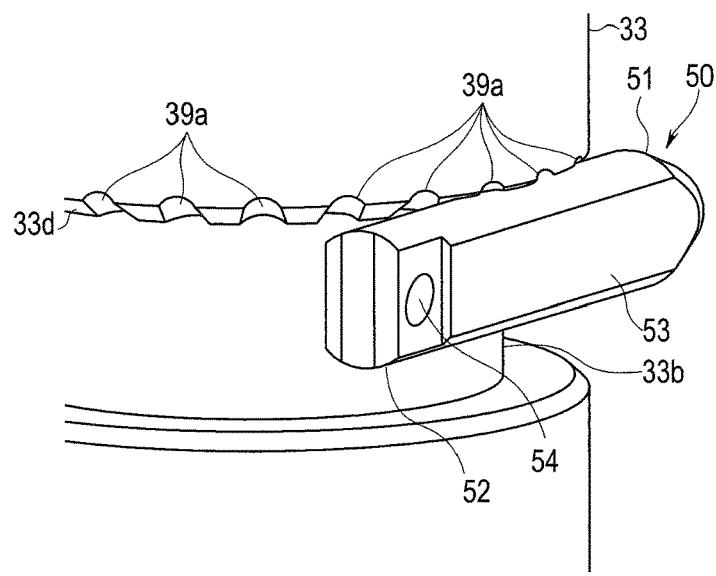
FIG. 21 relates to the third modification and is a perspective view showing a state that the image pickup unit is fixed with the fixing pin.
Figure 22:
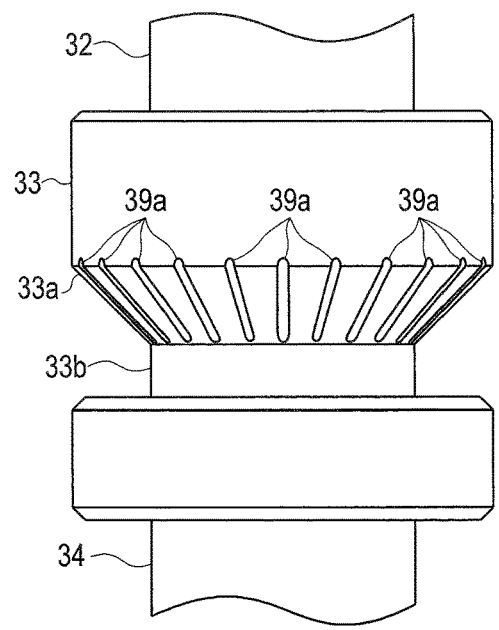
FIG. 22 relates to a fourth modification and is a side view showing a configuration of the body portion of the lens frame of the image pickup unit.
Figure 23:
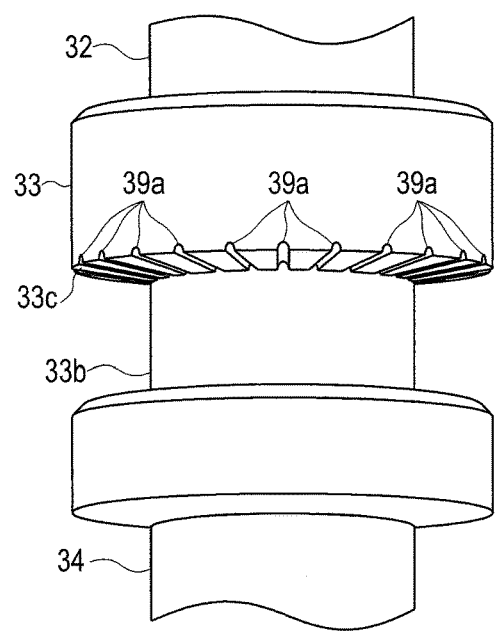
FIG. 23 relates to a fifth modification and is a perspective view showing a configuration of the body portion of the lens frame of the image pickup unit.
Figure 24:
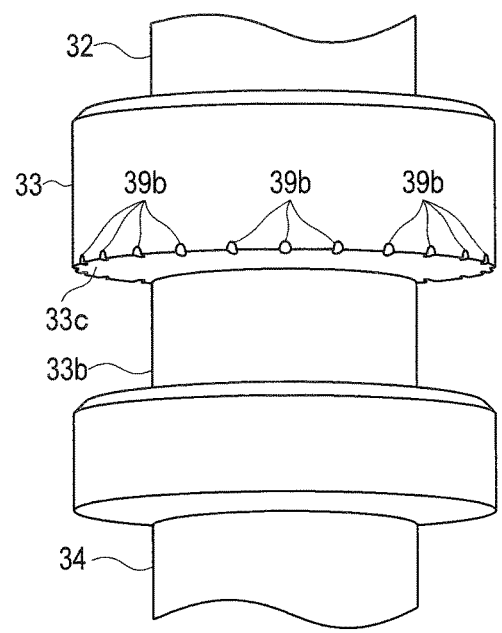
FIG. 24 relates to a sixth modification and is a perspective view showing a configuration of the body portion of the lens frame of the image pickup unit.
Figure 25:
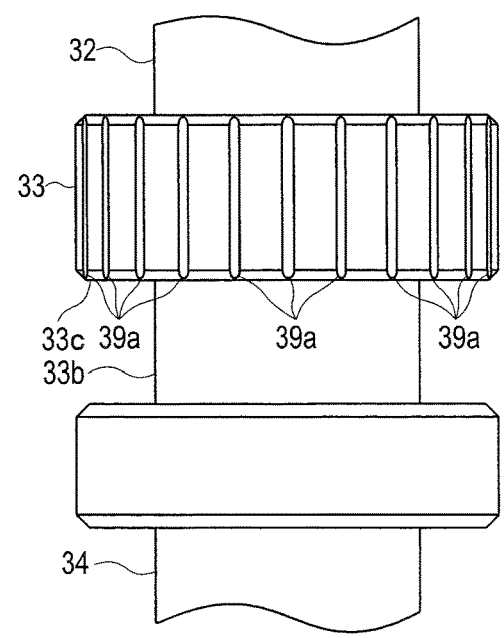
FIG. 25 relates to a seventh modification and is a side view showing a configuration of the body portion of the lens frame of the image pickup unit.

First, a parts fixing structure of an endoscope of an aspect of the present invention will be described based on drawings. FIG. 1 is a perspective view showing a whole configuration of an endoscope apparatus; FIG. 2 is a side view of an image pickup unit; FIG. 3 is a front view of the image pickup unit of FIG. 2 seen from an arrow III; FIG. 4 is a IV-IV line cross-sectional view of the image pickup unit of FIG. 2; FIG. 5 is a perspective view showing a distal end portion of the image pickup unit; FIG. 6 is an exploded perspective view showing a state of fitting the image pickup unit to a distal end rigid portion; FIG. 7 is a perspective view showing a configuration of a fixing pin; FIG. 8 is a cross-sectional view showing the configuration of the fixing pin; FIG. 9 is a perspective view showing a configuration of a jig; FIG. 10 is a partial cross-sectional view showing a state that the fixing pin to be fixed to the image pickup unit is inserted into a distal end constituting portion; FIG. 11 is a perspective view showing a state before a head portion of the fixing pin projecting from a stepped portion of the distal end constituting portion is rotated with the jig; FIG. 12 is a perspective view showing a state that the jig is fitted in the head portion of the fixing pin; FIG. 13 is a perspective view showing a state that the fixing pin is rotated by the jig; FIG. 14 is a partial cross-sectional view showing a state that the fixing pin is rotated, and the image pickup unit is fixed to the distal end constituting portion; FIG. 15 is a perspective view showing a state that the image pickup unit is fixed with the fixing pin; FIG. 16 relates to a first modification and is a partial cross-sectional view showing a state that the fixing pin fixed to the image pickup unit is inserted in the distal end constituting portion; FIG. 17 is a partial cross-sectional view showing a state that the fixing pin is rotated, and the image pickup unit is fixed to the distal end constituting portion; FIG. 18 relates to a second modification and is a partial cross-sectional view showing a state that the fixing pin fixed to the image pickup unit is inserted in the distal end constituting portion; FIG. 19 is a partial cross-sectional view showing a state that the fixing pin is rotated, and the image pickup unit is fixed to the distal end constituting portion; FIG. 20 relates to a third modification and is a side view showing a configuration of a body portion of a lens frame of the image pickup unit; FIG. 21 is a perspective view showing a state that the image pickup unit is fixed with the fixing pin; FIG. 22 relates to a fourth modification and is a side view showing a configuration of the body portion of the lens frame of the image pickup unit; FIG. 23 relates to a fifth modification and is a perspective view showing a configuration of the body portion of the lens frame of the image pickup unit; FIG. 24 relates to a sixth modification and is a perspective view showing a configuration of the body portion of the lens frame of the image pickup unit; FIG. 25 relates to a seventh modification and is a side view showing a configuration of the body portion of the lens frame of the image pickup unit; and FIG. 26 relates to an eighth modification and is a perspective view showing a configuration of the body portion of the lens frame of the image pickup unit.

As shown in FIG. 1, an electronic endoscope system 1 of the present embodiment is configured mainly with an electronic endoscope (hereinafter simply referred to as an endoscope) 2, a light source apparatus 3, a video processor 4 and a monitor 5.

The endoscope 2 is configured having an elongated insertion portion 9, an operation portion 10, and a universal cable 19 which is an electric cable. The insertion portion 9 of the endoscope 2 is configured having a distal end portion 6, a bending portion 7 and a flexible tube portion 8 from a distal end in that order.

On the operation portion 10, a bending operation knob 14 for performing a bending operation of the bending portion 7 of the insertion portion 9 is rotatably arranged, and switches and the like for various kinds of endoscope functions are provided. Note that the bending operation knob 14 is such that a UD bending operation knob 12 for performing a bending operation of the bending portion 7 in upper and lower directions and an RL bending operation knob 13 for performing a bending operation of the bending portion 7 in left and right directions are arranged being overlapped with each other.

Further, a coupling portion between the insertion portion 9 and the operation portion 10 is configured having a grasping portion 11, which is a portion grasped by a user, and a treatment instrument channel insertion portion 18 arranged at a bend preventing portion provided between the grasping portion 11 and one end of the flexible tube portion 8 of the insertion portion 9 to be an opening of a treatment instrument channel through which various kinds of treatment instruments provided on the insertion portion 9.

The universal cable 19 extended from the operation portion 10 has an endoscope connector 19a attachable to detachable from the light source apparatus 3 at an extension end. Note that the endoscope 2 of the present embodiment transmits illuminating light from the light source apparatus 3 to the distal end portion 6 by a light guide bundle (not shown) which is illuminating means arranged in the universal cable 19, the operation portion 10 and the insertion portion 9.

Further, a coiled cable 20 is extended from the endoscope connector 19a, and an electric connector which is attachable to and detachable from the video processor 4 is provided at an extension end of the coiled cable 20.

The video processor 4 is electrically connected to the monitor 5 which displays an endoscopic image and performs signal processing of an image pickup signal photoelectrically converted by an endoscope image pickup unit 30 to be described later, which is image pickup means of the endoscope 2 to be described later. Note that, in the electronic endoscope system 1, the light source apparatus 3 is provided with an air/water feeding function of ejecting air and water from the distal end portion 6 of the insertion portion 9 of the endoscope 2 though it is not shown.

The distal end portion 6 includes an endoscope image pickup unit (hereinafter simply referred to as an image pickup unit) 30 shown in FIGS. 2 to 5.

As shown in FIGS. 2 to 4, the image pickup unit 30 has an objective lens unit 38, an image pickup device holding frame 35 and a reinforcing frame 36, and an image pickup cable 37 extends from a proximal end of the reinforcing frame 36.

The objective lens unit 38 has a substantially tubular lens frame 31. The image pickup device holding frame 35 is fitted onto rear of the lens frame 31. The reinforcing frame 36 is fitted onto rear of the image pickup device holding frame 35.

Here, the lens frame 31 is made of metal, such as stainless steel. As shown in FIG. 4, the lens frame 31 is a lens fixing frame holding an objective lens group 41, which is an objective optical system, and is configured having an observation window holding portion 32, a body portion 33 in such an outward flange shape that a diameter of an outer circumferential part is larger than the observation window holding portion 32, and a fitted portion 34 connected to the body portion 33 and fitted by being pressed by a distal end part of the image pickup device holding frame 35, in that order from a distal end side.

The observation window holding portion 32 of the lens frame 31 holds an objective lens 41a which is arranged at a most distal end of the objective lens group 41 to be an observation window (see FIGS. 3 and 4). On the body portion 33 of the lens frame 31, a circumferential groove 33b, which has a slope portion 33a as a contact surface formed in a circumferential direction on a distal end side, is formed as shown in FIGS. 2, 4 and 5.

As shown in FIGS. 2 and 4, the slope portion 33a here is a partial conical surface inclined by a predetermined acute angle θ, for example, 45° (θ=45°) in an inner diameter direction toward a proximal end side, relative to a front-back direction of the image pickup unit 30.

That is, the circumferential groove 33b is in such a shape that the acute slope portion 33a having the predetermined angle θ, for example, 45° relative to a longitudinal axis X (see FIG. 2) along the front-back direction of the image pickup unit 30 is formed on the distal end side so that inclination in the inner diameter direction toward the proximal end side is obtained. Note that the slope portion 33a is not limited to a straight cross section but may be a convex curved surface or a concave curved surface.

The image pickup device holding frame 35 fitted onto the lens frame 31 holds an optical member 42 at a proximal end portion (see FIG. 4). On a rear surface of the optical member 42, a front surface of cover glass 43 is fixed with optical adhesive. On a rear surface of the cover glass, a solid image pickup device 44, which is image pickup means such as a CCD and a CMOS, is fixed with the optical adhesive.

The solid image pickup device 44 is electrically connected to an image pickup substrate 45. The optical member 42 held by the image pickup device holding frame 35, the solid image pickup device 44 and the image pickup substrate 45 are covered with the reinforcing frame 36. Circumferences of the solid image pickup device 44 and the image pickup substrate 45 is covered with filling agent (not shown) such as adhesive in the reinforcing frame 36.

In the image pickup unit 30 configured as described above, a photographing light (an object image) of an optical axis O (see FIG. 4) incident on the objective lens group 41 is formed on a receiving portion of the solid image pickup device 44. The solid image pickup device 44 photoelectrically converts the photographing light and outputs image pickup data of an object to the image pickup substrate 45.

Then, the image pickup substrate 45 electrically processes the image pickup data appropriately and outputs the data to an electrically connected communication cable (not shown). The communication cable is inserted and arranged in the endoscope 2 and electrically connected to the video processor 4, which is an external apparatus, via the electric connector provided on the coiled cable 20 extending from the endoscope connector 19a.

By the way, the distal end portion 6 of the insertion portion 9 is provided with a distal end constituting portion 21 as a distal end portion body (a distal end member) which is a substantially cylindrical-shaped block made of synthetic resin here, which is shown in FIG. 6. In the distal end constituting portion 21, a unit installation hole portion 22 into which the image pickup unit 30, which is a functional member here, is inserted is formed. On a distal end side of the unit installation hole portion 22, an observation hole portion 22a into which the observation window holding portion 32 of the image pickup unit 30 is inserted.

Then, the image pickup unit 30 is inserted into the unit installation hole portion 22 from a proximal end side, and fitted and fixed so as to be in a state that a front surface of the body portion 33 projecting to an outer diameter direction is caused to be in contact with a rear end surface of the distal end constituting portion 21 which is located and steppedly formed at a rear end of the observation hole portion 22a and forms the unit installation hole portion 22.

Here, a parts fixing structure of the endoscope for fixing the image pickup unit 30 to the distal end constituting portion 21 provided on the distal end portion 6 in the present embodiment will be described below in detail.

In one side periphery portion of the distal end constituting portion 21 which is a first fixed member here, a unit fixing hole portion 23 is formed in a manner of corresponding to a position where the slope portion 33a of the body portion 33 is arranged when the image pickup unit 30, which is a second fixed member here, is fitted, the unit fixing hole portion 23 being made such that its intermediate portion and the unit installation hole portion 22 communicate with each other in an inner diameter direction of the distal end constituting portion 21.

Note that the unit fixing hole portion 23 is formed in the distal end constituting portion 21 so as to be orthogonal to the longitudinal axis X of the image pickup unit 30 and in a tangential direction relative to an outer circumferential portion of the lens frame 31 when the image pickup unit 30 is fitted. In other words, the unit fixing hole portion 23 is formed so as to be orthogonal to a hole axis of the unit installation hole portion 22 and have a hole axis in the tangential direction relative to the slope portion 33a of the image pickup unit 30 arranged in the unit installation hole portion 22.

On the distal end constituting portion 21, such a step portion 24 that a cross section forms an L shape along a longitudinal direction is formed on an outer circumferential portion where an opening of the unit fixing hole portion 23 is formed. On the step portion 24, an arc-shaped recess portion 24a having a curvature radius larger than that of the unit fixing hole portion 23 and wall surface portions 24b and 24c along a longitudinal direction in a front-back direction of the recess portion 24a are formed.

A fixing pin 50 as a fixing member for fixing the image pickup unit 30 to the distal end constituting portion 21 is inserted into the unit fixing hole portion 23 formed in the distal end constituting portion 21. That is, the image pickup unit 30 and the distal end constituting portion 21 constitute fixed members which are fixed to each other by the fixing pin 50.

Note that the fixing pin 50 here is formed with metal softer than the metal (stainless steel) used for the lens frame 31 of the image pickup unit 30, for example, stainless steel of a kind with lower hardness than the kind of the stainless steel used for the lens frame 31, or phosphor bronze.

As shown in FIGS. 7 and 8, the fixing pin 50 has a pin body 51 and a head portion 52 formed at one end of the pin body 51. The pin body 51 is obtained by D-cutting a cylindrical rod body so that its cross section is in a D shape, and a plane portion 53 as a contactless portion is formed on a part of an outer circumference along a longitudinal axis direction.

On the head portion 52, two plane portions 52a having a predetermined width and being parallel to each other are formed, and the head portion 52 has a hole portion 54 made to pass through the two plane portions 52a. Note that the fixing pin 50 is a member to be exchanged each time of use (disposable).

Further, a predetermined axial rotation direction is specified with respect to the unit fixing hole portion 23, and the fixing pin 50 is rotated to fix the image pickup unit 30 to the distal end constituting portion 21 after being inserted. At this time, a jig 60 as shown in FIG. 9 is used to rotate the fixing pin 50.

A distal end portion 61 of the jig 60 is provided with a recess portion 63 on which two arm portions 62 are formed in a manner of having two facing surfaces. Further, a cylindrical body 64 having a larger diameter relative to the distal end portion 61 is fitted onto the distal end portion 61 in the jig 60, and the jig 60 has a projecting portion 65 extended from a part of a distal end of the cylindrical body 64.

The jig 60 configured as described above is used at time of rotating the fixing pin 50 around an axis by the head portion 52 of the fixing pin 50 being engageably inserted into the recess portion 63 so that the facing surfaces of the two arm portions 62 come into surface-contact with the plane portions 52a of the head portion 52.

Here, the configuration of fixing the image pickup unit 30 to the distal end constituting portion 21 in the endoscope 2 of the present embodiment will be described below in detail.

First, an observation window holding portion 32 side of the lens frame 31 of the image pickup unit 30, which is a distal end side, is inserted and fitted into the unit installation hole portion 22 from a rear side of the distal end constituting portion 21 (see FIG. 6).

Then, when the observation window holding portion 32 of the image pickup unit 30 is inserted into the observation hole portion 22a, and the front surface of the body portion 33 is caused to come into contact with an end surface of the distal end constituting portion 21 forming the unit installation hole portion 22.

After that, the image pickup unit 30 is rotated and adjusted to be at a predetermined position set in advance according to a direction of a photographing image to be acquired (an upward, downward, left or right direction) relative to the distal end constituting portion 21.

The circumferential groove 33b formed on the body portion 33 of the image pickup unit 30 arranged in the unit installation hole portion 22 as described above is located at the intermediate portion of the unit fixing hole portion 23. At this time, the slope portion 33a formed on the distal end side of the circumferential groove 33b is in a state of being located within the intermediate portion of the unit fixing hole portion 23, in the unit installation hole portion 22.

In this state, the fixing pin 50 is inserted into the unit fixing hole portion 23 of the distal end constituting portion 21 from a pin body 51 side. At this time, the pin body 51 of the fixing pin 50 is inserted into the unit fixing hole portion 23 by adjusting a position of rotation around the axis so that the plane portion 53 contactlessly faces the slope portion 33a of the image pickup unit 30, as shown in FIG. 10.

Further, the fixing pin 50 is in a state that the head portion 52 projects from the step portion 24 of the distal end constituting portion 21 as shown in FIG. 11. Note that a predetermined length to be included within the recess portion 24a is set for the fixing pin 50, relative to a length of the unit fixing hole portion 23, so that the head portion 52 projects at the step portion 24 of the distal end constituting portion 21 and does not project from the outer circumferential portion of the distal end constituting portion 21.

In this state, the head portion 52 is fitted into the recess portion 63 of the jig 60 so that the head portion 52 of the fixing pin 50 is sandwiched between the two arm portions 62 provided on the distal end portion 61 of the jig 60. Note that a position of the jig 60 around a longitudinal axis is adjusted so that the distal end portion 61 is fitted into the recess portion 24a formed at the step portion 24 of the distal end constituting portion 21, and the facing planes of the two arm portions 62 come into surface-contact with the respective plane portions 52a of the head portion 52 of the fixing pin 50.

That is, such similar curvature radiuses are set that an outer circumferential shape of the distal end portion 61 of the jig 60 and a shape of the recess portion 24a having a semicircular shaped cross section formed at the step portion 24 of the distal end constituting portion 21 are substantially same. At this time, the jig 60 is in a state that one side wall surface of the projecting portion 65 projecting from the cylindrical body 64 toward a distal end portion 61 side is in contact with a wall surface portion 24b of the step portion 24 of the distal end constituting portion 21.

Note that the jig 60 is set so that, in a state that the fixing pin 50 is inserted in the unit fixing hole portion 23, and the plane portion 53 of the fixing pin 50 is in contact with the slope portion 33a of the body portion 33 of the image pickup unit 30, one side wall surface of the projecting portion 65 is in contact with the wall surface portion 24b of the step portion 24 of the distal end constituting portion 21 in accordance with a position where the recess portion 63 of the distal end portion 61 to be fitted over the head portion 52 is formed.

That is, as for the jig 60, a position of the projecting portion 65 relative to the distal end portion 61 having the two arm portions 62 and the recess portion 63 is set so that, when the head portion 52 is fitted into the recess portion 63 before the fixing pin 50 is rotated, one side wall surface of the projecting portion 65 comes into contact with the wall surface portion 24b of the step portion 24 of the distal end constituting portion 21.

Next, the jig 60 is rotated until the other side wall surface of the projecting portion 65 comes into contact with a wall surface portion 24c of the step portion 24 of the distal end constituting portion 21 as shown in FIG. 13 from the state of FIG. 12. Thereby, the fixing pin 50 is rotated around the axis by the predetermined angle θ, 90° to 135° here.

Note that, for the jig 60, the predetermined angle θ (90° to 135°), which is an amount of rotation around the axis of the fixing pin 50, is determined by the other side wall surface of the projecting portion 65 projecting from the cylindrical body 64 to the distal end portion 61 side coming into contact with the wall surface portion 24c of the step portion 24 of the distal end constituting portion 21.

That is, for the jig 60, a length (width) around the axis of the projecting portion 65 is set so that the predetermined angle θ (90° to 135°), which is the amount of rotation of the fixing pin 50, is determined by the other side wall surface of the projecting portion 65 coming into contact with the wall surface portion 24c of the step portion 24 from the state that one side wall surface of the projecting portion 65 is in contact with the wall surface portion 24b of the step portion 24 of the distal end constituting portion 21.

Then, an intermediate portion of the rotated fixing pin 50 comes into contact with the slope portion 33a, and is deformed (plastically deformed) to be a recess-shaped deformed portion 51a as shown in FIGS. 14 and 15. That is, since the fixing pin 50 is formed with the metal with lower hardness than the rigid metal forming the body portion 33 of the image pickup unit 30, the fixing pin 50 is easily deformed without damaging the slope portion 33a of the body portion 33. In this way, the image pickup unit 30 is assembled and fixed to the distal end constituting portion 21.

At this time, by the fixing pin 50 deformed (plastically deformed) by the slope portion 33a of the body portion 33, the image pickup unit 30 is assembled and fixed to the distal end constituting portion 21 in a state that a stress Fa of pressing the image pickup unit 30 to the distal end side and a stress Fb of pressing the image pickup unit 30 to the inner diameter direction are given.

Thus, by providing the body portion 33 with the slope portion 33a into which the fixing pin 50 comes into contact with when the image pickup unit 30 is fixed to the distal end constituting portion 21, the image pickup unit 30 can be fixed at a predetermined position without backlash because a distal end side end surface of the body portion 33 is caused to come into contact with an end surface around a rear end of the observation hole portion 22a forming the unit installation hole portion 22 of the distal end constituting portion 21 by receiving the thrust-direction stress Fa to the distal end side, and an outer circumference surface of the body portion 33 is caused to come into contact with the inner circumference surface of the unit installation hole portion 22 toward one direction away from the fixing pin 50 by receiving the radial-direction stress Fb in the inner diameter direction.

Note that, when the recess-shaped deformed portion 51a (see FIG. 15) formed on the fixing pin 50 is closely in contact with the slope portion 33a and is in a state of being caught in a direction orthogonal to a longitudinal direction of the image pickup unit 30, that is, the axial direction of the fixing pin 50, and the plane portion 53 of the pin body 51 is not rotated to an original position facing the slope portion 33a, the fixing pin 50 is prevented from coming out from the unit installation hole portion 22.

Further, various kinds of units are similarly fixed to the distal end constituting portion 21 though the units are not shown here, and a distal end cover made of resin is fixed to a front portion. Furthermore, an outer cover is fixed to the distal end constituting portion 21 from a proximal end of the distal end cover by bobbin bonding or the like.

By the way, at time of pulling out the fixing pin 50 from the unit installation hole portion 22, it is only necessary that the plane portion 53 of the pin body 51 is rotated to the original position facing the slope portion 33a by the jig 60 as described above. At this time, in a state that one side wall surface of the projecting portion 65 of the jig 60 is in contact with the wall surface portion 24b of the step portion 24 of the distal end constituting portion 21, the plane portion 53 of the pin body 51 is at a position facing the slope portion 33a. When the fixing pin 50 is pulled out from the unit installation hole portion 22, the fixing pin 50 can be pulled out by putting a tool such as a hook in the hole portion 54 formed in the head portion 52.

As described above, in the endoscope parts fixing structure of the present embodiment, by providing the body portion 33 to be a position where the image pickup unit 30 is fixed, with the slope portion 33a with which the fixing pin 50 comes into contact, it is possible to arrange a center O1 of the fixing pin 50 at a position close to an inner diameter side of the image pickup unit 30, and it is not necessary to increase the outer diameter of the body portion 33. As a result, downsizing becomes possible.

Further, by causing the center O1 of the fixing pin 50 to be located in the circumferential groove 33b formed on the body portion 33 of the lens frame 31 of the image pickup unit 30, it is possible to fix the image pickup unit 30 to the distal end constituting portion 21 more stably.

Furthermore, in the endoscope parts fixing structure described above, since the fixing pin 50 to be inserted and fixed in a tangential direction of a fixation position of the body portion 33, here, the outer circumferential portion of the body portion 33 is used as a fixing member for fixing the image pickup unit 30 to the distal end constituting portion 21, a degree of positional freedom of a fixation position by the fixing pin 50 increases, and a thickness of the distal end constituting portion 21 can be suppressed. Thereby, the distal end constituting portion 21 can be downsized. As a result, downsizing becomes possible, and the distal end portion 6 can be also downsized, which leads to decrease in a diameter of the insertion portion 9 of the endoscope 2.

That is, since a configuration of performing fixation using set screws or the like as done conventionally is a configuration in which a fixing member is inserted in a direction toward a center (an inner diameter direction) of the distal end constituting portion 21, a position where a thickness of the distal end constituting portion 21 can be secured is restricted, and a certain degree of thickness is required. Therefore, the distal end constituting portion 21 is upsized.

In comparison, in the endoscope parts fixing structure of the present embodiment, the thickness of the distal end constituting portion 21 required for the fixing member is not required in comparison with the configuration in which fixation is performed with use of set screws. Therefore, the fixation position by the fixing pin 50 is not restricted so much, and the distal end constituting portion 21 can be downsized. As a result, the position where the image pickup unit 30 is fixed to the distal end constituting portion 21 is not restricted, and, therefore, a degree of freedom of arranging a fixation position of the image pickup unit 30 increases.

Further, in the endoscope parts fixing structure of the present embodiment, since the fixing pin 50 is formed with material with hardness lower than that of a position where the image pickup unit 30 is fixed, the image pickup unit 30 is not damaged. Therefore, difficulty in reuse of the image pickup unit 30 does not easily occur.

First Modification

Here, the body portion 33 of the lens frame 31 of the image pickup unit 30 may be a plane portion 33c as a contact surface orthogonal to the longitudinal direction of the image pickup unit 30 as shown in FIGS. 15 and 16 instead of the distal-end-side slope portion 33a forming the circumferential groove 33b.

In such a configuration, the intermediate portion of the fixing pin 50 rotated by the jig 60 comes into contact with the plane portion 33c and is deformed (plastically deformed).

At this time, by the fixing pin 50 deformed (plastically deformed) by the plane portion 33c of the body portion 33, the image pickup unit 30 is assembled and fixed to the distal end constituting portion 21 in a state that only the stress Fa of pressing the image pickup unit 30 to the distal end side is given.

In the configuration, it is possible to increase contact area without changing interference dimensions between the plane portion 53 of the fixing pin 50 and the plane portion 33c of the image pickup unit 30.

As a result, though a rotation torque of the fixing pin 50 at time of fixing the image pickup unit 30 to the distal end constituting portion 21 increases, fixing force for fixing the image pickup unit 30 with the fixing pin 50 also increases, and, therefore, the image pickup unit 30 becomes difficult to rotate around the longitudinal direction and can be stably fixed.

Second Modification

Here also, a distal end side of the body portion 33 of the lens frame 31 of the image pickup unit 30, which forms the circumferential groove 33b, is the plane portion 33c orthogonal to the longitudinal direction of the image pickup unit 30 as shown in FIGS. 17 and 18. In addition, the fixing pin 50 may have a cut-off surface 55 having two plane portions forming a substantially right angle, which is obtained by cutting the pin body 51 so that an L-shaped cross section is obtained, instead of the plane portion 53.

Even in such a configuration, by the fixing pin 50 deformed (plastically deformed) by the plane portion 33c of the body portion 33 of the image pickup unit 30, the image pickup unit 30 can be stably assembled and fixed to the distal end constituting portion 21 in the state that only the stress Fa of pressing the image pickup unit 30 to the distal end side is given.

Furthermore, though a fixing structure for fixing the image pickup unit 30 to the distal end constituting portion 21 has been described above, this is not limiting. In a case of fixing an illumination unit in which an illumination optical system is arranged, a channel unit for a treatment instrument channel, or a nozzle unit for air/water feeding or the like, to the distal end constituting portion 21 as a functional member of an endoscope also, a similar parts fixing structure can be applied.

Further, the fixing pin 50 may have a configuration in which, instead of the head portion 52, a slot is formed at one end portion, for example, so that the fixing pin 50 can be rotated by a minus driver.

Third Modification

In an endoscope parts fixing structure of the present modification, a chamfered portion 33d as a contact surface obtained by slightly shaving a corner portion on a circumferential groove 33b side of the body portion 33 is formed instead of the slope portion 33a of the body portion 33 provided on the lens frame 31 of the image pickup unit 30 as shown in FIG. 20.

A plurality of recess-shaped groove portions 39a are formed on the chamfered portion 33d so as to form a radial shape toward an inner diameter side of the lens frame 31. That is, unevenness is formed on a surface of the chamfered portion 33d by the plurality of groove portions 39a.

When the image pickup unit 30 here is fixed to the distal end constituting portion 21, the intermediate portion of the fixing pin 50 rotated by the jig 60 comes into contact with the chamfered portion 33d, which is uneven-shaped by the plurality of groove portions 39a, and is deformed (plastically deformed) as shown in FIG. 21.

Thereby, in the endoscope parts fixing structure of the present modification, the image pickup unit 30 is fixed to the distal end constituting portion 21 in a state that the fixing pin 50 is engaged with the uneven-shaped chamfered portion 33d and large friction occurs, and, therefore, the image pickup unit 30 becomes difficult to rotate around the longitudinal direction and can be more stably fixed. That is, the chamfered portion 33d here constitutes a friction surface having an uneven shape.

Fourth Modification

Note that, as shown in FIG. 22, the plurality of recess-shaped groove portions 39a may be radially formed similarly to the third modification on the slope portion 33a of the body portion 33 provided on the lens frame 31 of the image pickup unit 30 so that a surface of the slope portion 33a becomes uneven-shaped.

When the image pickup unit 30 here is fixed to the distal end constituting portion 21 also, the intermediate portion of the fixing pin 50 rotated by the jig 60 comes into contact with the slope portion 33a, which is uneven-shaped by the plurality of groove portions 39a, and is deformed (plastically deformed), though this is not shown.

At this time, in the endoscope parts fixing structure of the present modification also, the image pickup unit 30 is fixed to the distal end constituting portion 21 in a state that the fixing pin 50 is engaged with the uneven-shaped slope portion 33a and large friction occurs, and, therefore, the image pickup unit 30 becomes difficult to rotate around the longitudinal direction and can be more stably fixed. That is, the slope portion 33a here constitutes a friction surface having an uneven shape.

Fifth Modification

As shown in FIG. 23, an endoscope parts fixing structure of the present modification is configured such that the plane portion 33c as a contact surface orthogonal to a longitudinal direction of the lens frame 31 is formed instead of the slope portion 33a of the body portion 33 provided on the lens frame 31 of the image pickup unit 30 similarly to the first and second modifications, and a plurality of recess-shaped groove portions 39a similar to those of the third and fourth modifications are radially formed on the plane portion 33c. That is, unevenness is formed on the surface of the plane portion 33c by the plurality of groove portions 39a.

When the image pickup unit 30 here is fixed to the distal end constituting portion 21, the intermediate portion of the fixing pin 50 rotated by the jig 60 comes into contact with the plane portion 33c, which is uneven-shaped by the plurality of groove portions 39a, and is deformed (plastically deformed), though this is not shown.

At this time, the image pickup unit 30 is fixed to the distal end constituting portion 21 with the fixing pin 50 in a state that the fixing pin 50 is engaged with the uneven-shaped plane portion 33c and large friction occurs. Therefore, in the endoscope parts fixing structure of the present modification also, the image pickup unit 30 becomes difficult to rotate around the longitudinal direction and can be more stably fixed. That is, the plane portion 33c here constitutes a friction surface having an uneven shape.

Sixth Modification

Note that, instead of the plurality of recess-shaped groove portions 39a formed on the plane portion 33c of the body portion 33 provided on the lens frame 31 of the image pickup unit 30 described in the fifth modification, a plurality of recess portions 39b may be formed in a circumferential direction of an edge portion of the plane portion 33c so that unevenness may be formed only on a corner portion of the plane portion 33c, as shown in FIG. 24.

Thereby, in the endoscope parts fixing structure of the present modification also, the image pickup unit 30 is fixed to the distal end constituting portion 21 in a state that the fixing pin 50 is engaged with an edge portion of the uneven-shaped plane portion 33c and large friction occurs, though this is not shown, and, therefore, the image pickup unit 30 becomes difficult to rotate around the longitudinal direction and can be more stably fixed. That is, the plane portion 33c here constitutes a friction surface having an uneven-shaped edge portion.

Seventh Modification

Further, as shown in FIG. 25, the plurality of groove portions 39a along the longitudinal direction of the lens frame 31 may be formed on the outer circumferential surface of the body portion 33 provided on the lens frame 31 of the image pickup unit 30 so that unevenness may be formed on the corner portion of the plane portion 33c.

Thereby, in the endoscope parts fixing structure of the present modification also, the image pickup unit 30 is fixed to the distal end constituting portion 21 in the state that the fixing pin 50 is engaged with an edge portion of the uneven-shaped plane portion 33c and large friction occurs, though this is not shown, and, therefore, the image pickup unit 30 becomes difficult to rotate around the longitudinal direction and can be more stably fixed. That is, the plane portion 33c here also constitutes a friction surface having an uneven-shaped edge portion.

Eighth Modification

Figure 26:
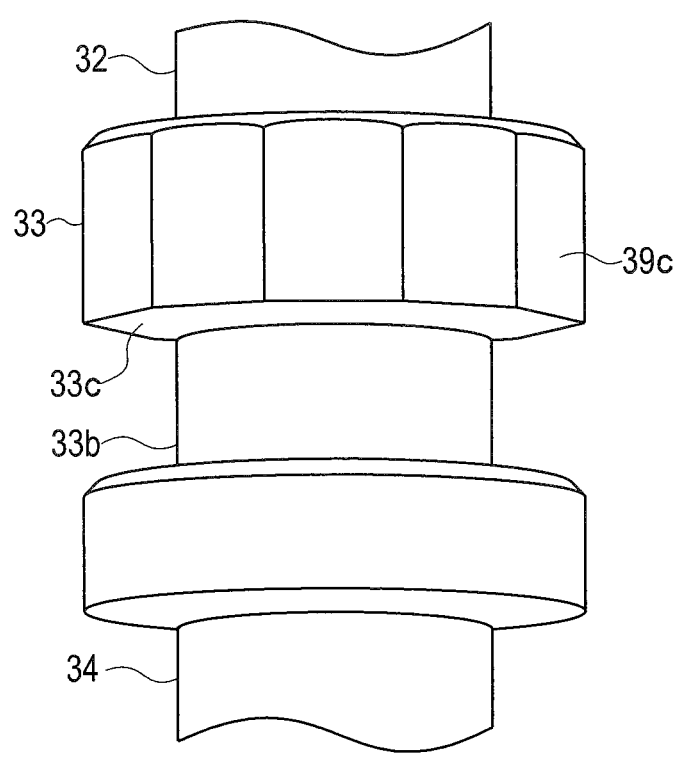
FIG. 26 relates to an eighth modification and is a perspective view showing a configuration of the body portion of the lens frame of the image pickup unit.

Furthermore, instead of the plurality of recess-shaped groove portions 39a or the plurality of recess portions 39b formed on the plane portion 33c of the body portion 33 provided on the lens frame 31 of the image pickup unit 30 described in the fifth to seventh modifications, a plurality of planes 39c may be formed around an outer circumference of the body portion 33 so that a cross-sectional shape of the plane portion 33c may be a polygonal shape, and unevenness may be formed on the edge portion of the plane portion 33c, as shown in FIG. 26.

Thereby, in the endoscope parts fixing structure of the present modification also, the image pickup unit 30 is fixed to the distal end constituting portion 21 in the state that the fixing pin 50 is engaged with an edge portion of the uneven-shaped plane portion 33c and large friction occurs, though this is not shown, and, therefore, the image pickup unit 30 becomes difficult to rotate around the longitudinal direction and can be more stably fixed. That is, the plane portion 33c here also constitutes a friction surface having an uneven-shaped edge portion.

Note that though the planes 39c have to be formed only on an outer circumferential end portion of the body portion 33 adjoining the plane portion 33c because it is sufficient if the plane portion 33c can be polygonal-shaped, the planes 39c are formed on the entire outer circumferential portion of the body portion 33 in consideration of workability, in the present modification.

The invention described in the above embodiment is not limited to the embodiment and the modifications. At a stage of implementation, various other modifications can be performed within a range not departing from the spirit of the invention. Furthermore, the above embodiment includes inventions at various stages, and various inventions can be extracted from appropriate combinations of the plurality of disclosed constituent features.

For example, when the stated problem can be solved and the stated effect can be obtained even if some constituent features are deleted from all the constituent features shown in the embodiment, a configuration after the constituent features are deleted can be extracted as an invention.

What is claimed is:

1. An endoscope comprising:
   a functional member having a contact surface formed on a part of an outer circumference of the functional member;
   a distal end member provided on a distal end portion of an insertion portion to be inserted into a subject, the distal end member comprising:
   a first hole having a first axis, the functional member being arranged in the first hole, and a second hole having a second axis, the second axis being orthogonal to the first axis and the second axis being offset from the first axis in a radial direction of the functional member, the second hole extending in a tangential direction relative to the contact surface of the functional member arranged in the first hole and the second hole communicating with the first hole; and a fixing member configured to generate a fixing force for fixing the functional member to the distal end member by being inserted into the second hole, the fixing member comprising:

a first portion for mating engagement with the contact surface of the functional member when the fixing member is inserted into the second hole; and a second portion having an interference fit with the contact surface of the functional member when the fixing member is inserted into the second hole and rotated around the second axis by a predetermined angle;

wherein the functional member is fixed to the distal end member when the fixing member is rotated around the second axis by the predetermined angle.

2. The endoscope according to claim 1, wherein the second portion of the fixing member comes into contact with the contact surface and is deformed by the fixing member being rotated around the second axis.

3. The endoscope according to claim 1, wherein the functional member is fixed to the distal end member with the fixing member pressing the functional member towards a distal end side of the distal end member.

4. The endoscope according to claim 3, wherein
the contact surface is a slope portion formed having a predetermined angle in an inner diameter direction toward a proximal end side of the functional member; and the functional member is fixed with the fixing member in a manner of being pressed to the distal end side and an inner diameter side of the distal end member by the fixing member being in contact with the slope portion.

5. The endoscope according to claim 1, wherein the first portion of the fixing member is planarly formed along a longitudinal direction from a cylindrical rod body.

6. The endoscope according to claim 1, wherein material forming the fixing member has a hardness lower than a hardness of material forming the contact surface of the functional member.

7. The endoscope according to claim 1, wherein the distal end member having a wall surface for determining an amount of rotation of a jig configured to rotate the fixing member, the wall surface being formed on an outer circumference portion where an opening of the second hole is formed.

8. The endoscope according to claim 1, wherein the contact surface has a friction surface configured to give friction force to the functional member.

9. The endoscope according to claim 8, wherein the friction surface has grooves or unevenness.

10. The endoscope according to claim 1, wherein the functional member is an image pickup unit for picking up an image of the subject.

* * * * *